US011914015B2

(12) United States Patent
Shoji et al.

(10) Patent No.: US 11,914,015 B2
(45) Date of Patent: Feb. 27, 2024

(54) MAGNETIC RESONANCE IMAGING APPARATUS AND IMAGE PROCESSING METHOD

(71) Applicant: Hitachi, Ltd., Tokyo (JP)

(72) Inventors: Hiroki Shoji, Tokyo (JP); Toru Shirai, Tokyo (JP); Shinji Kurokawa, Tokyo (JP)

(73) Assignee: FUJIFILM HEALTHCARE CORPORATION, Chiba (JP)

(*) Notice: Subject to any disclaimer, the term of this patent is extended or adjusted under 35 U.S.C. 154(b) by 443 days.

(21) Appl. No.: 17/205,238

(22) Filed: Mar. 18, 2021

(65) Prior Publication Data

US 2021/0333347 A1    Oct. 28, 2021

(30) Foreign Application Priority Data

Apr. 28, 2020 (JP) .................................. 2020-079606

(51) Int. Cl.
*G01R 33/56* (2006.01)
*G16H 30/40* (2018.01)

(52) U.S. Cl.
CPC ..... *G01R 33/5608* (2013.01); *G01R 33/5602* (2013.01); *G06T 3/4084* (2013.01); *G16H 30/40* (2018.01)

(58) Field of Classification Search
CPC ............ G01R 33/5608; G01R 33/5602; G06T 3/4084; G16H 30/40; G16H 30/20; A61B 5/055; A61B 5/0033; A61B 5/7203

(Continued)

(56) References Cited

U.S. PATENT DOCUMENTS 8,781,197 B2 * 7/2014 Wang ..................... G01R 33/54
382/131
2018/0338701 A1 * 11/2018 Amemiya .............. A61B 5/055
(Continued)

FOREIGN PATENT DOCUMENTS

JP     2005-160107 A    6/2005
JP     2005160107 A  *  6/2005  ........... G06T 3/4084
(Continued)

OTHER PUBLICATIONS

Japanese Office Action received in corresponding Japanese Application No. 2020-079606 dated Aug. 15, 2023.

*Primary Examiner* — Juan A Torres
(74) *Attorney, Agent, or Firm* — Mattingly & Malur, PC

(57) ABSTRACT

Provided is a magnetic resonance imaging apparatus with no occurrence of artifacts, even after noise removal by applying Wavelet transform to a zero-fill reconstructed image. Nuclear magnetic resonance signals acquired by the magnetic resonance imaging apparatus are processed to perform reconstruction with a reconstruction matrix extended by zero-filling an acquisition matrix, and then a zero-fill reconstructed image is produced. This reconstructed image is subjected to an iterative operation combining the Wavelet transform and L1 norm minimization to remove noise. Before the noise removal, a pre-processing is performed to change the reconstruction matrix size so that an artifact does not occur in the image after noise removal, an artifact portion appears outside the reconstruction matrix after the noise removal, or cutting out is performed so that no artifact appears after the noise removal. The matrix size is restored to its original size in the post-processing after the noise removal.

8 Claims, 14 Drawing Sheets

(58) Field of Classification Search
USPC .......................................................... 382/128
See application file for complete search history.

(56) References Cited

U.S. PATENT DOCUMENTS

2020/0258199 A1    8/2020  Shirai et al.
2020/0271744 A1*   8/2020  Yamamoto ....... G01R 33/56509

FOREIGN PATENT DOCUMENTS

| JP | 2013-78569  A  |   | 5/2013 |              |
|----|----------------|---|--------|--------------|
| JP | 2013078569  A  | * | 5/2013 | ............... A61B 6/00 |
| JP | 2019-042444 A  |   | 3/2019 |              |
| JP | 2019042444  A  | * | 3/2019 | ............ A61B 5/055 |
| WO | 2019/179838 A1 |   | 9/2019 |              |

* cited by examiner

MAGNETIC RESONANCE IMAGING APPARATUS AND IMAGE PROCESSING METHOD

INCORPORATION BY REFERENCE

The present application claims priority from Japanese patent application JP-2020-079606 filed on Apr. 28, 2020, the content of which is hereby incorporated by reference into this application.

BACKGROUND OF THE INVENTION

Field of the Invention

The present invention relates to a magnetic resonance imaging apparatus (hereinafter, referred to as MRI apparatus), and more particularly, it relates to a technique for eliminating artifacts after removing noise of an image, the artifacts being caused by the noise removal.

Description of the Related Art

An MRI apparatus is a noninvasive medical imaging diagnostic equipment utilizing nuclear magnetic resonance phenomena in which hydrogen atomic nuclei (protons) placed in a static magnetic field resonate to high frequency magnetic field of a specific frequency. Since MRI can capture images of various tissue contrast depending on imaging methods and imaging parameter change, it is possible to acquire information on biological functions such as blood flow and metabolic function besides morphological information, and thus it is indispensable diagnostic equipment in the image diagnosis field.

One of the technical problems in the MRI is a shortening of the imaging time. Various shortening methods have been proposed, but shortening the imaging time is accompanied by a decrease in the signal-to-noise ratio (SNR). Therefore, a method for removing noise is also researched and developed at the same time. Among them, a noise removal method using Wavelet transform is generally used. For example, in Japanese Unexamined Patent Application Publication No. JP-A-2019-42444 (hereinafter referred to as Patent Document 1), it is described to use a Wavelet transform image for L1 norm minimization as a constraint of sparsity in noise removal of an image obtained by parallel imaging (PI).

In the MRI apparatus, position information is imparted to a nuclear magnetic resonance signal generated from a subject, using an encoded gradient magnetic field, and measurement data comprising the received nuclear magnetic resonance signals is arranged in the k-space with the direction of the encoding as an axial direction. The k-space is usually a square matrix, because an image is reconstructed by Fourier transform of the k-space data, and the measurement data is arranged to match this matrix. In MRI, there is an imaging method of filling the k-space asymmetrically for reduction of the imaging time and prevention of artifacts. Even in that case, in order to obtain an image of a square reconstruction matrix, zero-fill reconstruction is performed to fill the insufficient area of the k-space with zero. In addition, for the purpose of improving the apparent resolution, the zero-fill reconstruction such as extending the k-space more than twice is also generally performed. When performing such zero-fill reconstruction, a characteristic pattern appears when performing the Wavelet transform as noise removal, and such pattern may cause an artifact in the course of reconstruction. Since this artifact occurs in the whole image, the image quality deteriorates remarkably.

The present invention aims to solve the problem of the artifacts caused in the image when the zero-fill reconstruction is combined with noise removal using the Wavelet transform.

SUMMARY OF THE INVENTION

To solve the problem of artifacts, the present invention focuses on the fact that the artifact generated when combining zero-fill reconstruction with noise removal using the Wavelet transform, is inherent in high-frequency components of an image, with a characteristic of affecting the entire image, and the present invention performs a process so that such artifact does not appear in the image finally obtained.

The process of the present invention is broadly divided into two methods. First, an image obtained by the zero-fill reconstruction is subjected to pre-processing so that an artifact due to the Wavelet transform does not occur, or even if the artifact occurs, it can be eliminated by post-processing. Then, after noise removal by the subsequent Wavelet transform, the post-processing is performed so that the change performed by the pre-processing is restored. Another method is to predict and eliminate artifact signals during the noise removal process by the Wavelet transform.

That is, an MRI apparatus according to a first aspect of the present invention, comprises a measuring unit having a transmission unit configured to transmit an RF magnetic field pulse to a subject disposed in a static magnetic field, a receiving unit configured to receive a nuclear magnetic resonance signal generated by the subject, and a gradient magnetic field generator for providing a gradient magnetic field to the static magnetic field, and a computer configured to perform an operation on the nuclear magnetic resonance signal received by the receiving unit, wherein the computer comprises an image generator configured to process the nuclear magnetic resonance signal being received to generate a reconstructed image with a reconstruction matrix obtained by extending an acquisition matrix by zero-filling, and a noise remover configured to remove noise from the reconstructed image, wherein the noise remover performs noise removal after changing the size of a matrix of the reconstructed image, and performs a process of restoring the matrix of the reconstructed image after the noise removal, to the reconstruction matrix.

The second aspect of the MRI apparatus of the present invention comprises a measuring unit having a transmission unit configured to transmit an RF magnetic field pulse to a subject disposed in a static magnetic field, a receiving unit configured to receive a nuclear magnetic resonance signal generated by the subject, and a gradient magnetic field generator for providing a gradient magnetic field to the static magnetic field, and a computer configured to perform an operation on the nuclear magnetic resonance signal received by the receiving unit, wherein the computer comprises an image generator configured to process the nuclear magnetic resonance signal being received to generate a reconstructed image with a reconstruction matrix obtained by extending an acquisition matrix by zero-filling, and a noise remover configured to remove noise from the reconstructed image, wherein the noise remover includes an artifact prediction unit configured to predict characteristics of an artifact caused by generating the reconstructed image in the image generator and removing noise, and a window function creating unit configured to create a window function for eliminating the predicted artifact, and the artifact is eliminated by using the window function.

Further, the present invention provides the following image processing method. That is, there is provided an image processing method for performing noise removal in an image acquired by the MRI apparatus, wherein the image is reconstructed using a reconstruction matrix generated by extending an acquisition matrix of nuclear magnetic resonance signals by zero-filling, and the noise removal comprises a process of subjecting the reconstructed image to the Wavelet transform and an L1 norm minimization process, and the noise removal further comprises a process of changing a matrix size of the reconstructed image prior to the Wavelet transform, and a process of restoring the matrix size of the reconstructed image after the noise removal, or the image processing method further comprises a process of predicting a characteristic of an artifact caused by the reconstruction and the noise removal, a process of creating a window function for removing the predicted artifact, and a process of applying the created window function to the image after the L1 norm minimization.

According to the present invention, it is possible to eliminate the artifact caused by combining the zero-fill reconstruction with the noise removal using the Wavelet transform, to obtain a high-quality image.

BRIEF DESCRIPTION OF THE DRAWINGS

FIG. 2A illustrates the MRI apparatus of a vertical magnetic field system, FIG. 2B illustrates the MRI apparatus of a horizontal magnetic field system, and FIG. 2C illustrates the MRI apparatus with enhanced feeling of opening;

FIG. 9A is a flowchart of the processing of the pre-processing unit, and FIG. 9B is a flowchart of the processing of the post-processing unit;

DETAILED DESCRIPTION OF THE PREFERRED EMBODIMENT

First, an embodiment of an MRI apparatus to which the present invention is applied will be described.
[Outline of MRI Apparatus]

Figure 1:
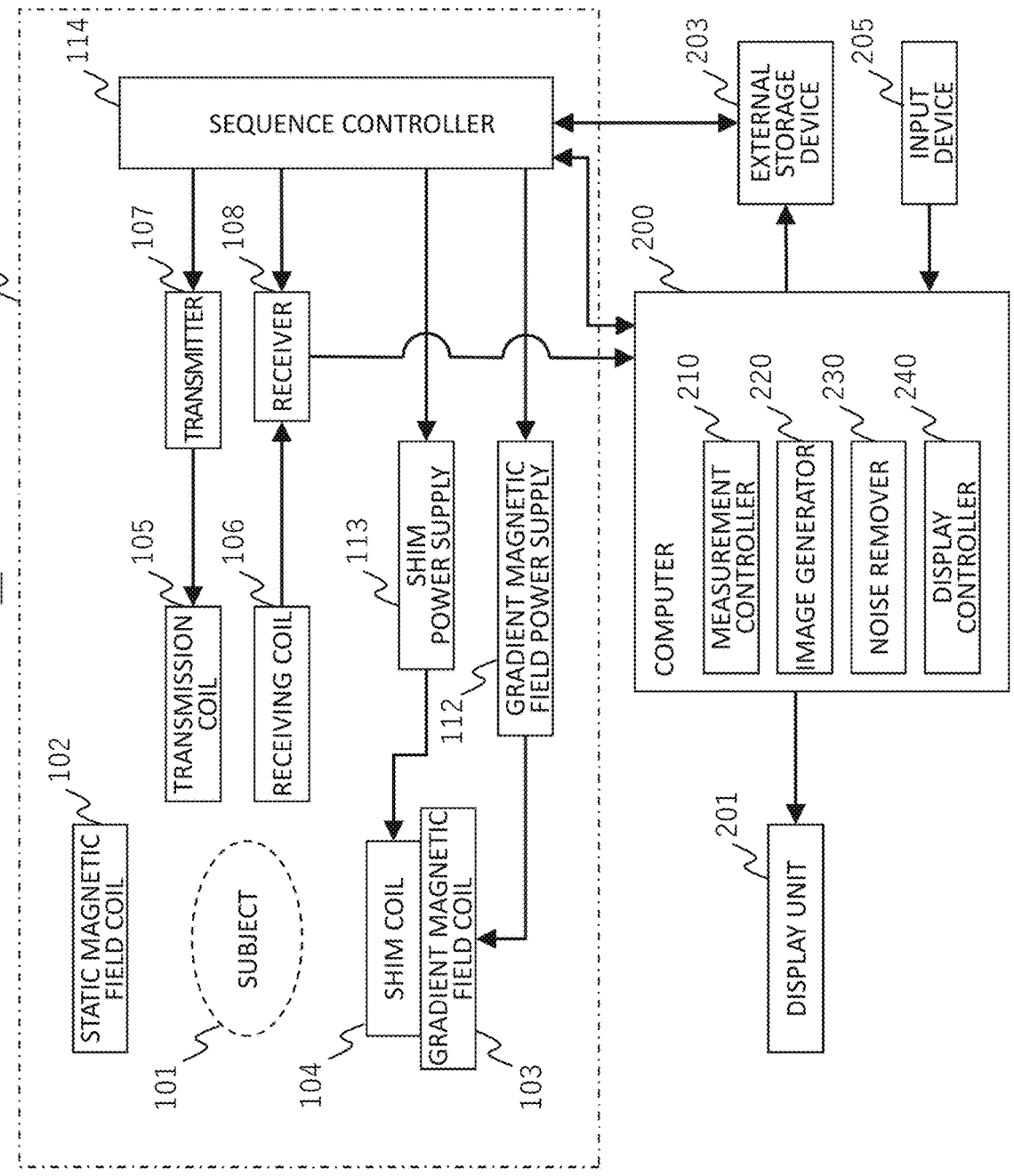
FIG. 1 is a block diagram illustrating a schematic configuration of an MRI apparatus in an embodiment of the present invention.

As shown in FIG. 1, an MRI apparatus 10 of the present embodiment broadly comprises a measurement unit 100 configured to measure a nuclear magnetic resonance signal generated from a subject 101, and a computer 200 configured to control the measurement unit 100 and to perform image reconstruction using the nuclear magnetic resonance signals measured by the measurement unit 100, and other calculations such as correction.

The measurement unit 100 includes a static magnetic field coil 102 for generating a static magnetic field in a space in which the subject 101 is placed, a transmission unit (105, 107) for transmitting an RF magnetic field pulse to the subject 101 disposed in the static magnetic field, a receiving unit (106, 108) configured to receive a nuclear magnetic resonance signal generated by the subject, and a gradient magnetic field coil 103 configured to provide a gradient magnetic field to the static magnetic field generated by the static magnetic field coil 102 to impart positional information to the nuclear magnetic resonance signal.

Figure 2A:
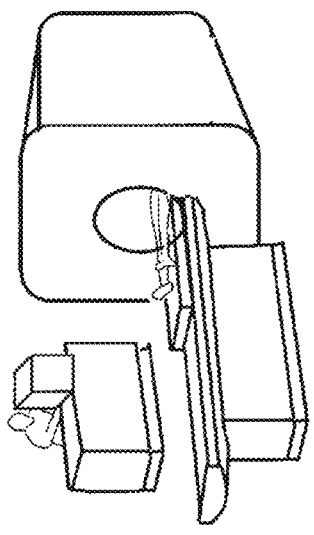
FIGS. 2A to 2C show external views of the MRI apparatus to which the present invention is applied.
Figure 2B:
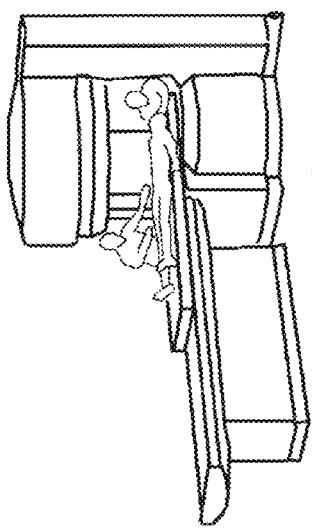
Figure 2C:
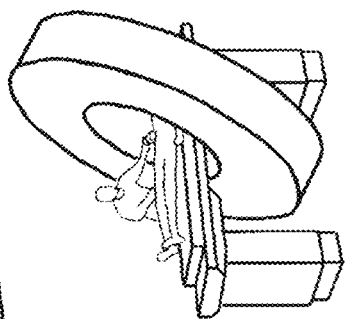

The static magnetic field coil 102 comprises a static magnetic field coil of a normal or superconducting type, a static magnetic field generating magnet, or the like, and according to the direction of the generated static magnetic field, there are a vertical magnetic field system and a horizontal magnetic field system. The shape of the coil and the appearance of the entire apparatus are different depending on the system. FIGS. 2A to 2C illustrate external views of the MRI apparatus of different systems. The present embodiment is applicable to any of the MRI apparatus as illustrated.

The transmission unit is provided with a transmission RF coil 105 (hereinafter, simply referred to as a transmission coil) for transmitting an RF magnetic field with respect to a measurement area of the subject 101, and a transmitter 107 having a high-frequency oscillator and an amplifier. The receiving unit includes a receiving RF coil 106 (hereinafter, simply referred to as a receiving coil) for receiving a nuclear magnetic resonance signal generated from the subject 101, and a receiver 108 including a quadrature detection circuit and an A/D converter. The receiving coil may be a multi-channel coil comprising a plurality of small receiving coils, in which case, the quadrature detection circuit and the A/D converter constituting the receiver 108 are connected to each of the coils. The nuclear magnetic resonance signal received by the receiver 108 is passed to the computer 200 as a complex digital signal.

The gradient magnetic field coil 103 has three sets of gradient magnetic field coils for applying a gradient magnetic field in the x-direction, y-direction, and z-direction, respectively, and each of the coils are connected to a gradient magnetic field power supply 112. Further, the MRI apparatus may include a shim coil 104 for adjusting a static magnetic field distribution, and the shim power supply 113 for driving the shim coil. Position information can be given to the nuclear magnetic resonance signal by the way the gradient magnetic field is applied.

The measurement unit 100 further includes a sequence controller 114 for controlling the operation of the measurement unit 100. The sequence controller 114 controls the operation of the gradient magnetic field power supply 112, the transmitter 107 and the receiver 108, to control the timing of the application of the gradient magnetic field, the RF magnetic field and the reception of the nuclear magnetic resonance signal. The time chart of the control is referred to as a pulse sequence, which is set in advance according to the measurement, and it is stored in a storage device or the like provided in the computer 200. The computer 200 controls the operation of the entire MRI apparatus 10, and performs various arithmetic processing on the received nuclear magnetic resonance signal. Specifically, the computer 200 is provided with function units, such as a measurement controller 210, an image generator 220 for reconstructing an image using the nuclear magnetic resonance signal, a noise remover 230 for removing noise of the image, and the display controller 240 for controlling a display such as an image on a display unit. In order to implement those functions, the computer 200 is provided with a CPU, a memory, a storage device, and others, and it is further connected to the display unit 201, an external storage device 203, an input device 205, and so on.

The display unit 201 is an interface for displaying results and others to an operator, the results being obtained by the arithmetic processing. The input device 205 is an interface for the operator (user) to input conditions, parameters, and so on, necessary for the measurement and arithmetic processing implemented in the present embodiment. The user can enter measurement parameters via the input device 205. The external storage device 203 holds, together with the storage device inside the computer 200, data used for various arithmetic processing executed by the computer 200, data obtained by arithmetic processing, inputted conditions, parameters, and so on.

The functions of each part of the computer 200 can be achieved as software incorporated in the computer 200, and the CPU loads the program (software) held by the storage device into the memory and executes the program. Various types of data used for processing each function and various types of data generated during processing are stored in the storage device or in the external storage device 203. Further, among the various functions implemented by the computer 200, at least one function may be implemented by an information processor being independent of the MRI apparatus 10, and capable of transmitting and receiving data to and from the MRI apparatus 10. For example, the function as the noise remover, which will be described later, may be implemented by a computer (an image processor) separated from the MRI apparatus. Alternatively, all or some of the functions may be implemented in hardware, such as ASIC (Application Specific Integrated Circuit), FPGA (Field programmable gate array), and others, rather than as software.

Imaging in the MRI apparatus 10 of the present embodiment is the same as commonly performed imaging, but the imaging includes zero-fill reconstruction in image generation using the measured nuclear magnetic resonance signals, and performs a Wavelet transform in the noise removal of the resulting image. In this situation, this imaging is characterized in carrying out the processing which does not cause an artifact originating from the zero-fill reconstruction and the Wavelet transform in the final image.

Figure 3:
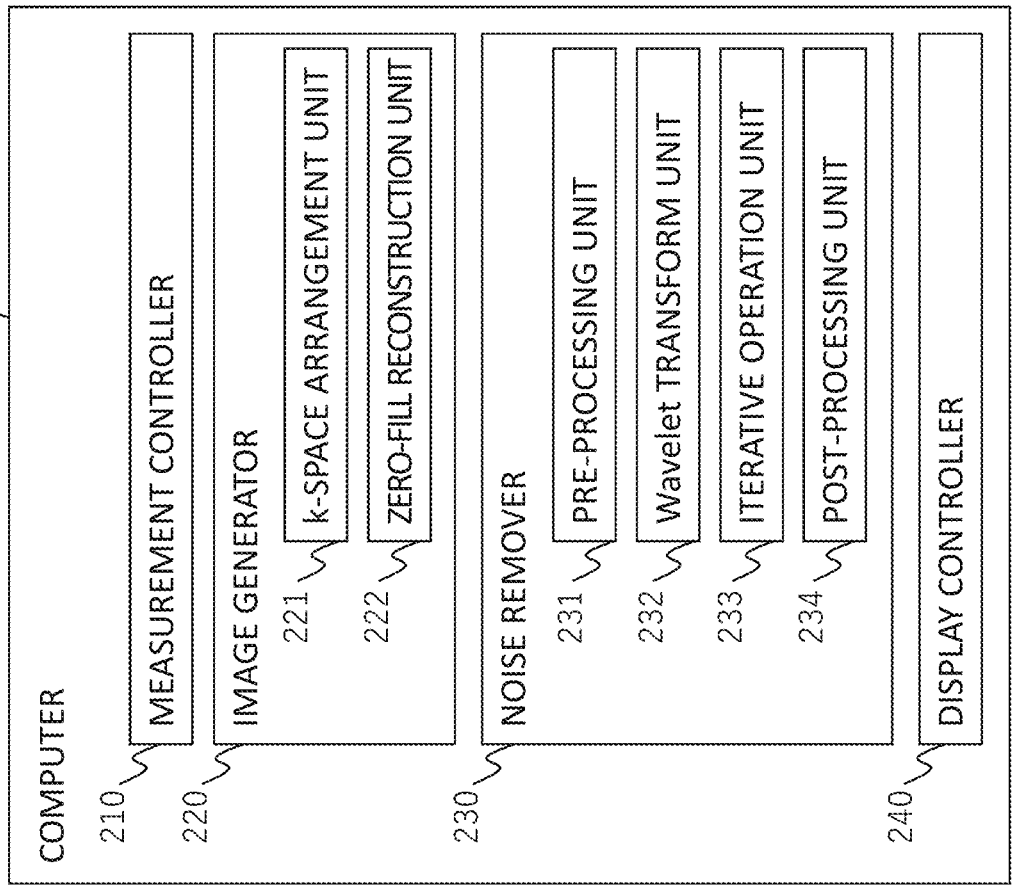
FIG. 3 is a functional block diagram of a computer according to an embodiment.

FIG. 3 shows an example of the computer 200 for performing such processing. As illustrated, the image generator 220 includes a k-space arrangement unit 221 for placing in the k-space measured data comprising the measured nuclear magnetic resonance signals, and a zero-fill reconstruction unit 222 for performing a predetermined zero-filling in the k-space data and then performing the Fourier transform of the k-space data to reconstruct an image. The noise remover 230 includes a Wavelet transform unit 232 and an iterative operation unit 233 that performs an operation of noise removing, a pre-processing unit 231 that performs a pre-processing to change a matrix size of the image generated by the image generator 220 prior to the Wavelet transform, and a post-processing unit 234 that performs processing such as restoring the image size to the size before the pre-processing. In the case where the functions of the noise remover are performed by another computer (the image processor) separated from the MRI apparatus, the image processor receives the image obtained by the zero-fill reconstruction, and performs processing of noise removal which will be described later.

Figure 4:
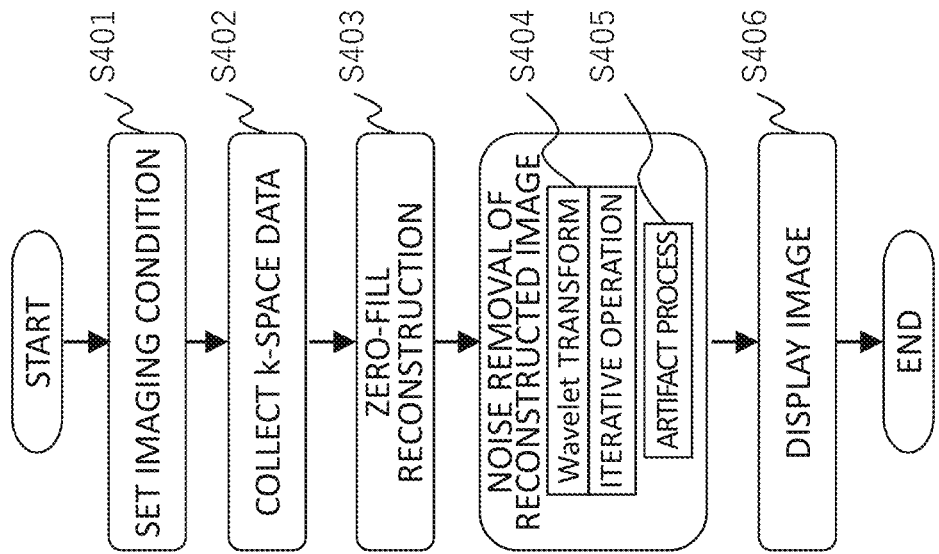
FIG. 4 is a flowchart of the processing performed by the computer according to an embodiment.

Next, there will be described the MRI apparatus 10 of the present embodiment, primarily the operation of the computer 200. FIG. 4 illustrates the operation.

First, the computer receives the setting of an imaging sequence and the imaging condition from the user via the input device 205 (S401). The imaging sequence is not particularly limited, and in order to reduce the imaging time, an imaging technique for measuring a spatially overlapped signal, for example, parallel imaging (PI), or simultaneous multi-slice imaging (SMS) may be selected for the setting. The imaging condition includes the parameters (repetition time TR and echo time TE) of the imaging sequence, and further includes the decimation (undersampling) rate when thinning measurement (PI) of the k-space is performed. In the case of the simultaneous multi-slice imaging (SMS), the number of slices is also provided. When these imaging conditions are set as the inspection protocol, the conditions set as the inspection protocol are read in.

The measurement controller 210 operates the sequence controller 114 in accordance with the pulse sequence provided based on parameters inputted by the user, and measures a nuclear magnetic resonance signal (echo signal) of a predetermined condition. The sequence controller 114 controls each unit of the MRI apparatus 100, according to an instruction from the measurement controller 210, whereby k-space data corresponding to an acquisition matrix based on the parameters are collected (S402). In the case where the acquisition matrix is a two-dimensional matrix, for example, the phase direction is determined by the phase encoding number, and the reading direction is determined by the number of sampling, and it is different from a reconstruction matrix (k-space data corresponding thereto) represented by a power of two. In the present embodiment, it is assumed that the zero-fill reconstruction is to be performed and the size of the acquisition matrix shall be smaller than the size of the reconstruction matrix.

Figure 5:
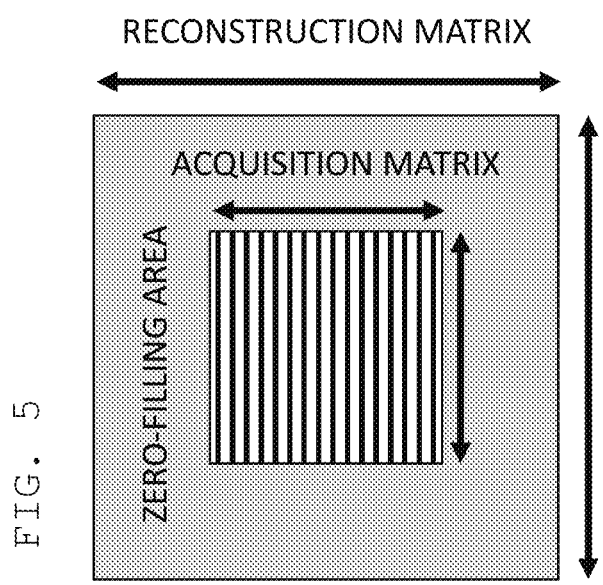
FIG. 5 illustrates a reconstruction matrix and an acquisition matrix.

The image generator 220 arranges the nuclear magnetic resonance signals in the k-space, and, as shown in FIG. 5, compensates for the insufficient area of the k-space data with zeros with respect to the reconstruction matrix (image space matrix), performs Fourier transform, and generates a reconstructed image (S403). As an example, FIG. 5 shows data in the two-dimensional direction, but it is also applicable to data only in one dimensional direction.

Then, the noise remover 230 performs a process for removing noise by the Wavelet transform and the iterative operation on the image data (S404). In this situation, a processing to eliminate artifacts caused by the noise removal, or a processing to prevent artifacts are performed (S405). Specific examples of the processing of noise removal and artifact elimination will be described in the embodiment in the following.

The reconstructed image after the noise removal may be stored in the external storage device 203 as required, or displayed on the display unit 201 by the display controller 240 (S406).

There will now be described embodiments of a specific processing of the noise remover 230.

Embodiment 1

In the present embodiment, utilizing the fact that an artifact caused by noise removal using the zero-fill reconstruction and Wavelet transform appears as a characteristic artifact in a high-frequency region of the k-space, a region is created where the artifact is made occur by extending k-space data of an image in a pre-processing, and then, processing of cutting this area is performed as a post-processing.

With reference to the flowchart of FIG. 6, the processing of the noise remover 230 in the present embodiment will be described. In the present embodiment, measurement data of the acquisition matrix smaller than the reconstruction matrix is also obtained, the measurement data is arranged in the k-space, and the zero-fill reconstruction is performed as in the processing of FIG. 4 (S601).

Figure 7:
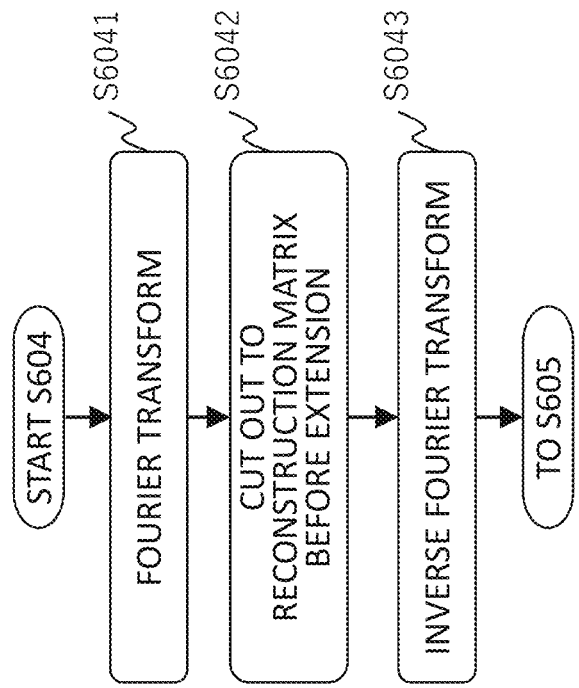
FIG. 7 is a flowchart of the processing of a pre-processing unit according to the first embodiment.

In the present embodiment, the pre-processing unit 231 (FIG. 3) performs the pre-processing on the image obtained by the zero-fill reconstruction, prior to the noise removal, and enlarges the size of the image (S602). Specifically, as shown in FIG. 7, the sizes of the two-dimensional acquisition matrix and the reconstruction matrix are obtained from the imaging parameters (S6021). The reconstructed image obtained in step S601 is subjected to Fourier-transform and converts data in the image space to k-space data (S6022), and the data is extended by zero-filling so as to exceed the size of the reconstruction matrix in the k-space (S6023). The extended k-space data is subjected to inverse-Fourier transform and it is converted from the k-space data to the image-space data (S6024).

The pre-processing yields image data larger in size than the original reconstructed image. The noise remover 230 performs noise removal on the pre-processed image (S603). The noise removal includes an L1-norm minimization process and iterations for error minimization, and uses the Wavelet transform for the L1-norm minimization process. Specifically, the process of minimizing the L1 norm is repeated on the Wavelet transformed image so as to minimize an error between an input image and an output image.

The Wavelet transform is a process of setting a mother wavelet as a reference and expanding/contracting and parallel translating the mother wavelet, thereby extracting waveforms of various scales similar to those in the waveform to be analyzed, and when applied to the image obtained by zero-filling the high-frequency region, waveforms that are not in the original image are extracted into the high-frequency region, resulting in occurrence of artifacts. In the present embodiment, a high-frequency component is extended by the pre-processing, whereby components that will become artifacts after noise removal can be aggregated to the high-frequency component. In the post-processing (S604), this high frequency components are cut out.

Figure 8:
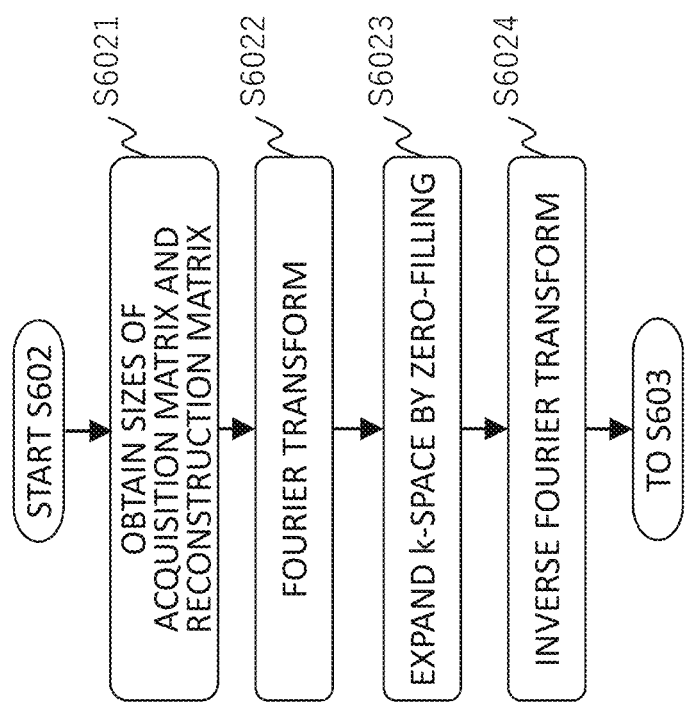
FIG. 8 is a flowchart of the processing of a post-processing unit according to the first embodiment.

As shown in FIG. 8, the post-processing unit 234 converts the noise-removed image from the image space data to k-space data by the Fourier transform (S6041), and cuts out the reconstruction matrix size that is the same as the size prior to extension in the k-space (S6042). Thus, the thus cut-out k-space data is transformed from the k-space to the image space by the inverse Fourier transform to obtain a reconstructed image (S6043). As described above, in the image after the noise removal, the occurrence of the artifact is moved or biased, outside the reconstruction matrix in the k-space, i.e., to a region extended by zero filling. Therefore, with this cutting into the reconstruction matrix by the post-processing, it is possible to eliminate or reduce the artifact.

In the pre-processing S602, the artifact reduction effects can be obtained, if the size of the matrix extended by zero-filing exceeds the size of the reconstruction matrix. For example, by using the matrix four times larger than the acquisition matrix, the occurrence of artifact can be moved out of the acquisition matrix.

Further, when the PI method for performing the thinning measurement of the acquisition matrix is adopted as the imaging method in the present embodiment, the size of the acquisition matrix used in the pre-processing (S602) and in the post-processing (S604) shall be the same as the size of the acquisition matrix that is used when the PI method is not applied (before thinning).

As described above, according to the present embodiment, in the pre-processing before noise removal, the k-space region of the image of interest is extended to be larger than the size of the reconstruction matrix and the k-space region is returned to the region in the image space, and then the noise removal is performed. This allows the occurrence of artifact caused by the Wavelet transform to move to the outside of the acquisition matrix, so that a reconstructed image with reduced artifacts or without artifacts can be obtained.

Embodiment 2

Figure 9B:
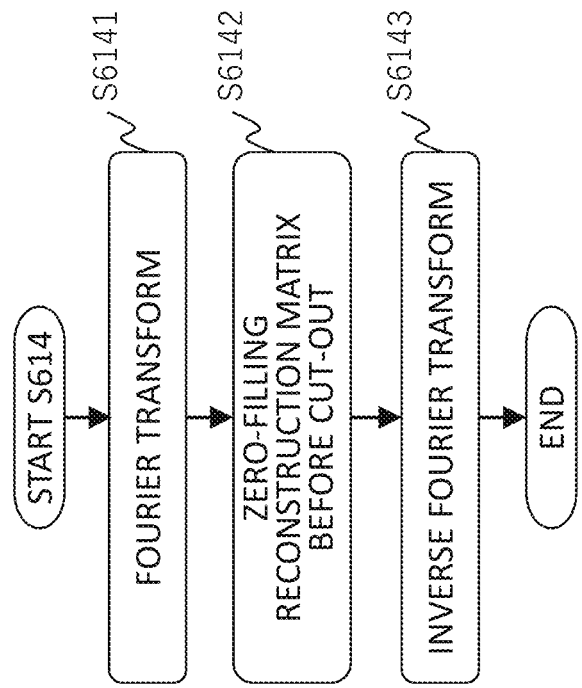
FIGS. 9A to 9B illustrate the processing of a second embodiment.
Figure 9A:
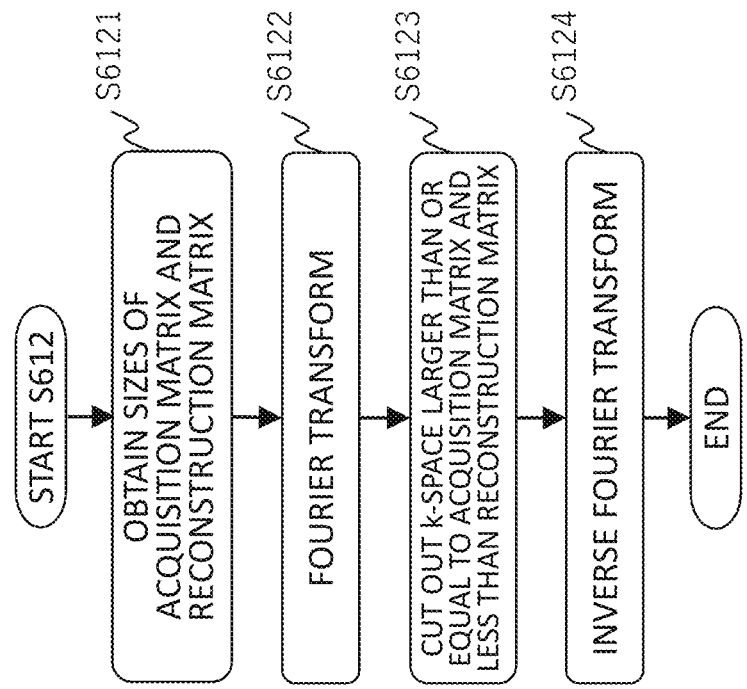

In the present embodiment, similar to Embodiment 1, the pre-processing of an image of interest is performed prior to noise removal, and after the noise removal, the post-processing is performed to restore the image to the original reconstruction matrix. In the present embodiment, however, it is featured that cutting out is performed to a size larger than or equal to the acquisition matrix and smaller than the reconstruction matrix in the pre-processing, and then in the post-processing, the size is restored to that of the original reconstruction matrix. Since the configuration and processing of the noise remover 230 are the same as those shown in FIGS. 3 and 6, the pre-processing S602 of FIG. 6 will be hereinafter referred to as S612, and the post-processing S604 will be referred to as S614, to describe the details. FIGS. 9A and 9B show the details of the pre-processing and the post-processing.

Figure 10:
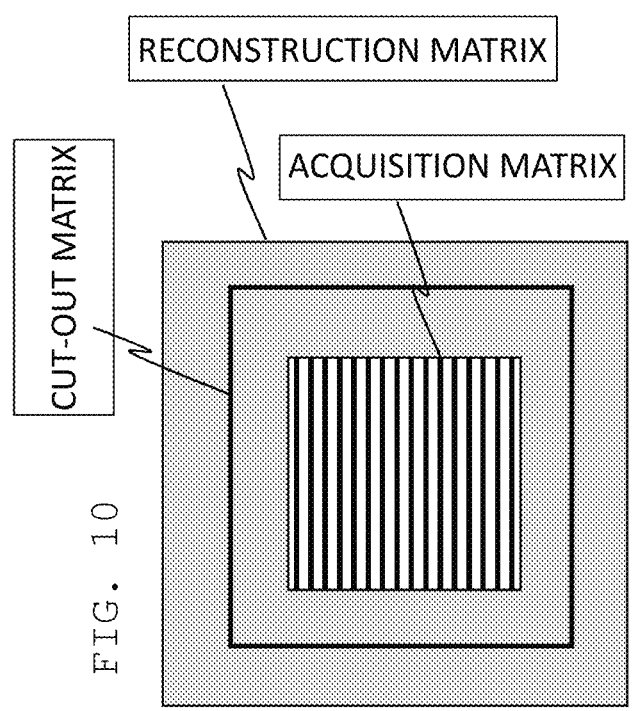
FIG. 10 illustrates cutting out of the matrix according to the second embodiment.

As shown in FIG. 9A, in the pre-processing (S612), the pre-processing unit 231 acquires the sizes of the two-dimensional acquisition matrix and the reconstruction matrix from the parameters (S6121). The image after the zero-fill reconstruction (S601) is Fourier-transformed and converted from the image space data to the k-space data (S6122). The high-frequency region of the k-space data is cut off, and as shown in FIG. 10, data is cut out so that the size of the k-space becomes the size of the acquisition matrix or more and less than the reconstruction matrix (S6123). Then, cut-out k-space data is inverse Fourier transformed and converted from the k-space data to the image space data (an image) (S6124).

By performing the process of cutting off the high-frequency region (S6123), it is possible to remove the components that are eventually included in the high-frequency region during zero-fill reconstruction, i.e., the components that are liable to be extracted erroneously during the Wavelet transform. The size being cut out in step S6123 is required to be less than the size of the reconstruction matrix, but the closer to the acquisition matrix is the size, the occurrence of artifacts can be prevented more effectively. The size to be cut out is not limited, for example, any size of the power of two may be selected, whereby the Fourier transform can be processed at high speed, resulting in improvement of the processing speed in the whole noise removal processing.

After the above process (S612), noise removal is performed (S603). The noise removal is the same process as that of the first embodiment, and the Wavelet transform unit 232 and the iterative operation unit 233 perform iterative operations of Wavelet transform and norm minimization on the pre-processed images.

The post-processing (S614) is the process of restoring the image having been downsized in the pre-processing, to the original. That is, as shown in FIG. 9B, the post-processing unit 234 converts the noise-removed image from the image space data to the k-space data by the Fourier transform (S6141), performs zero-filling in the k-space so as to obtain the reconstruction matrix size prior to cutting out (S6142), and then performs the inverse Fourier transform to convert the k-space data to the image space data (S6143).

According to the present embodiment, prior to the noise removal, high-frequency components generated during the Wavelet transform, the components causing artifacts, are removed from the image after zero-fill reconstruction, whereby it is possible to prevent the occurrence of artifacts in the noise removal (S603).

As described above, there have been described the embodiments of the method for preventing the occurrence of artifacts by performing the pre-processing on the zero-fill reconstructed image. In the following, there will be described an embodiment of a technique for eliminating artifacts in the process of the noise removal using the Wavelet transform.

Embodiment 3

In the present embodiment, it is featured that in the course of noise removal, a characteristic of artifact is extracted, and a filter for eliminating the artifacts is created, so as to remove only the artifact.

Figure 11:
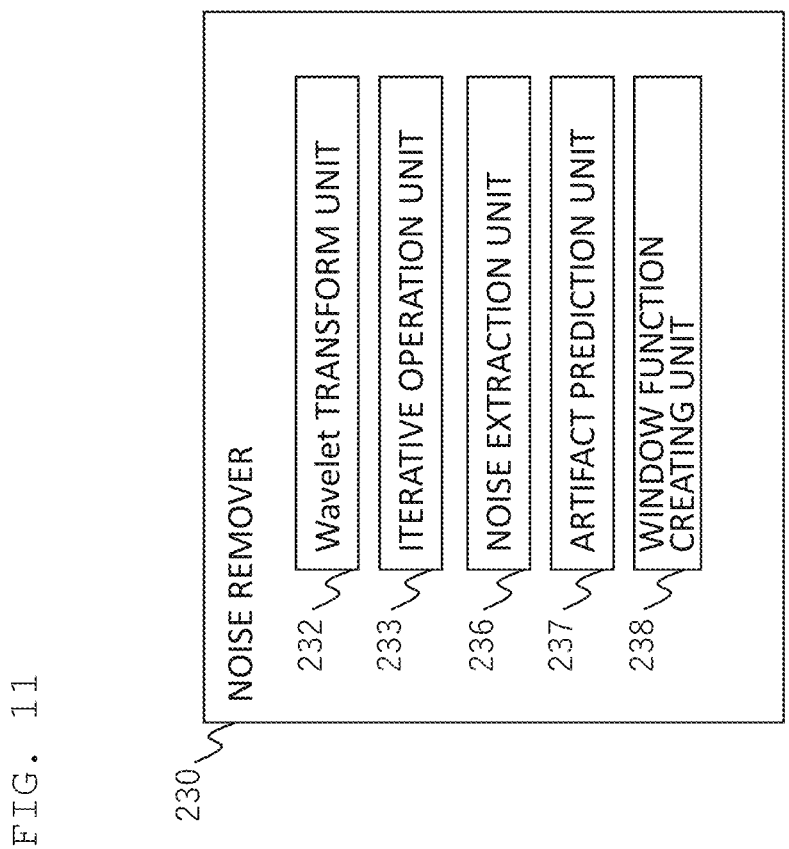
FIG. 11 is a functional block diagram of the computer according to a third embodiment.

FIG. 11 illustrates a configuration of the noise remover 230 of the present embodiment. In the present embodiment, the noise remover 230 includes, in addition to the Wavelet transform unit 232 and the iterative operation unit 233, a noise extracting unit 236 for extracting noise from an image after the Wavelet transform to create a noise image, an artifact prediction unit 237 for predicting an artifact signal from the noise image created by the noise extracting unit 236, and a window function creating unit 238 for creating a window function (filter) for eliminating the artifact.

Figure 12:
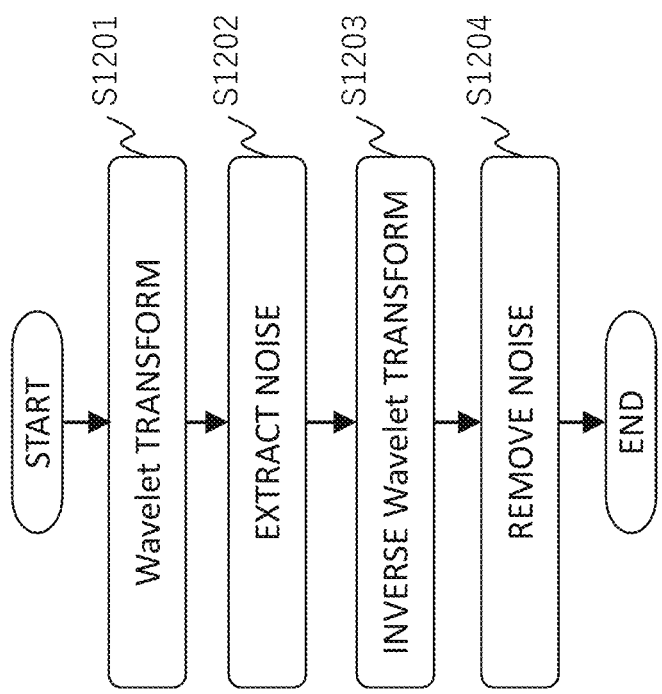
FIG. 12 is a flowchart of the processing of the noise remover according to the third embodiment

There will now be described the processing of the noise remover 230, mainly focusing on the processing of those units as mentioned above. FIG. 12 shows the outline of the processing.

In the present embodiment, as shown in FIG. 12, when the noise remover 230 receives the zero-fill reconstructed image, first, the Wavelet transform unit 232 performs the Wavelet transform on the image (S1201), performs L1-norm minimization processing to extract noise (S1202: noise extractor 236), and performs the inverse Wavelet transform on the extracted noise (Wavelet space data) to create a noise image (S1203). Noise removal is performed by subtracting the noise image created by step S1203 from the original image (zero-fill reconstructed image) (S1204). In the present embodiment, this noise removal step (S1204) not only simply subtracts the noise image from the original image, but also removes artifacts generated in the noise image. There are two methods for removing artifacts: one is performed in the k-space and the other is performed on the image. Either method may be adopted.

Figure 13:
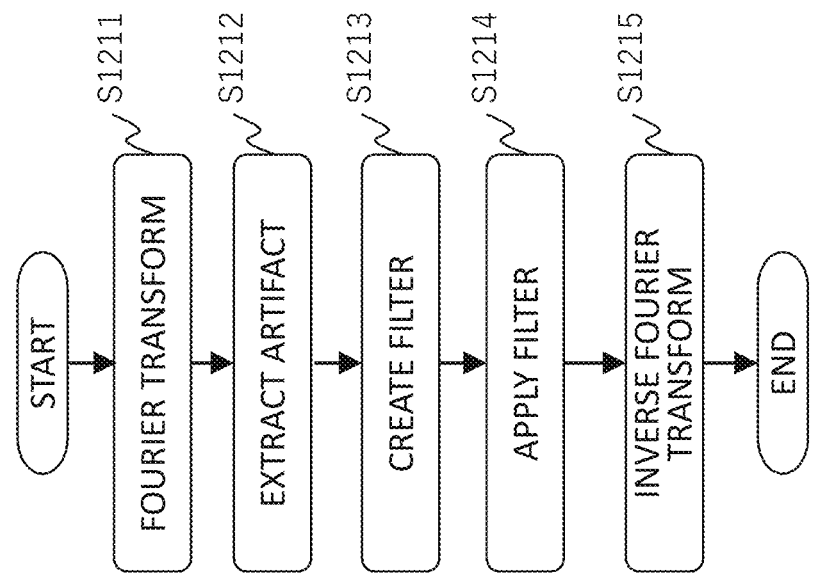
FIG. 13 illustrates an example of artifact elimination according to the third embodiment.

First, with reference to FIG. 13, a method for removing artifacts in the k-space will be described. This process is performed on an image that has been subjected to the inverse Wavelet transform after the L1 norm minimization process (step S1202 in FIG. 12), and the artifact is eliminated prior to adding the image to an input image in the iterative calculation of noise removal.

Specifically, the noise image obtained by the inverse Wavelet transform (S1203) is Fourier transformed, and converted from the image space data to k-space data (S1211). Then, signals of artifacts are extracted in the k-space (S1212). As described in the first embodiment, since the artifact signals are present in the high frequency region in the k-space, for example, a signal outside the acquisition matrix and larger than any threshold value in the k-space may be considered as an artifact, or the signal outside the acquisition matrix may be considered as an artifact, so as to extract the artifact signal.

Then, a filter to cancel this artifact signal is created (S1213), and this filter is applied to the k-space data (k-space data of the noise image) obtained by step S1211 (S1214). As the filter, an appropriate filter is created, considering the size and others of the acquisition matrix and the reconstruction matrix. For example, a rectangular function associated with the size of the acquisition matrix can be used. The rectangular function is a filter setting the acquisition matrix area as 1 and the outside of the acquisition matrix area as 0, which is most easily implemented and has a high effect of artifact elimination. When the ratio between the reconstruction matrix and the acquisition matrix is around 50%, the artifact elimination effect by the rectangular function may be reduced. In this case, for example, using a filter in which the high-frequency region (high region) changes smoothly, such as Fermi function is used. Such filter is applied to the k-space data, and thereafter it is restored as image data, whereby artifacts and noise can be eliminated.

Further, if only the artifacts extracted in step S1212 are to be eliminated, Sinc function or any Band-Pass filter may be applied to the k-space data of the noise image. For example, in the case of the Band-Pass filter, the artifact extracting part shall be 0 and the others shall be 1. If the Sinc function is employed, the Sinc function shall be obtained by changing the frequency so that the artifact extracting part becomes 0.

A filter to cancel the artifact signal as described above is created, the filter is applied to the k-space data, and the k-space data is transformed to image space data by the inverse Fourier transform (S1215). Then, the addition process to the original image is performed, and using the resultant image as the input image, the iterative operation of noise removal is performed to finally obtain an image in which the noise is removed. It is to be noted that instead of performing filtering on the noise image obtained for each repetition of the iterative operation as described above, the above-mentioned filter creation and the artifact elimination using the filter may be performed with respect to the noise image obtained at the end of the iterative operation.

Figure 14:
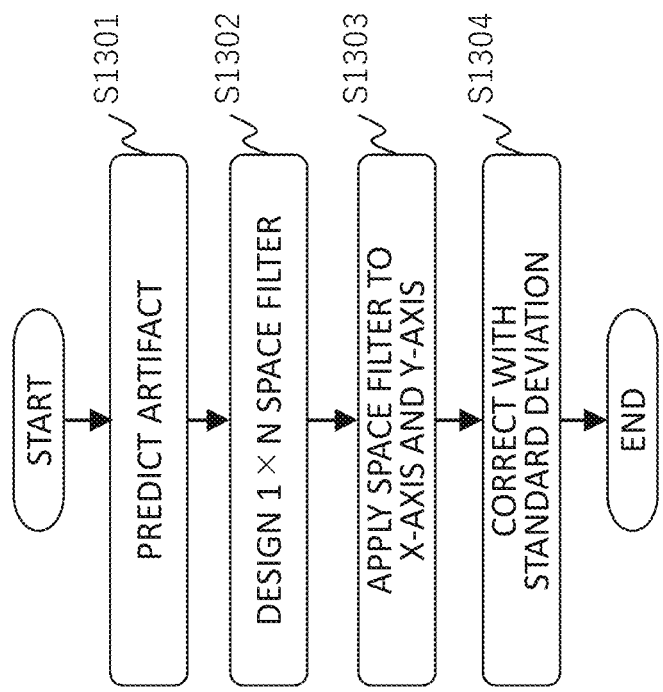
FIG. 14 illustrates another example of artifact elimination according to the third embodiment.

The above is the process of eliminating the artifact signal in the k-space during the noise removal process. In the following, with reference to FIG. 14, there will be described a method for eliminating an artifact on an image.

In this method, first, the prediction unit 237 predicts an artifact based on the information obtained from the noise image provided by the inverse Wavelet transform (S1203) (S1301). As a method of prediction of artifacts, for example, there is a method of empirically making database of the behaviors of artifacts relative to the ratio of the reconstruction matrix to the acquisition matrix. The behavior of artifact is, for example, information indicating which component of the image the artifact affects, depending on the ratio of the reconstruction matrix to the acquisition matrix, i.e., where in the high and mid-region the artifact appears. Such behaviors of artifacts may be accumulated from many image data, and stored in advance as a database in the external storage device 203 of the MRI device 10, or they may be stored in a storage means or in a cloud separate from the MRI device 10.

After predicting a characteristic of the artifact, the window function creating unit 238 creates a spatial filter of 1×N to minimize the artifact, based on the characteristic (S1302). In step S1301, as the characteristic of the artifact, it is possible to predict where in a frequency region from the mid to high region the components of the artifact are distributed. Then, the window function creating unit 238 decreases N when it is predicted they are distributed in the mid-region, whereas it increases N when it is predicted they are distributed in the high-region. Instead of newly creating a window function, the window function creating unit 238 may incorporate a standard window function that is easily implemented and has an artifact reduction effect, and adjust the size N of the standard window function according to the image quality. For example, 1×3 moving average filter [⅓, ⅓, ⅓] is convolved as the standard window function for each direction of the two dimensions. Since the blurring is increased in this case (N=3), the size of N may be adjusted according to the image quality to be obtained. A filter coefficient may be created to follow Gauss function or Sinc function, rather than a simple moving average.

Then, the noise remover 230 applies the window function (spatial filter) created by the window function creating unit 238, to the noise image obtained by the iterative operation in each direction of the two dimensions (S1303), to obtain an image in which noise and artifacts are removed.

Thereafter, the images before and after the spatial filtering are corrected so that values of the standard deviations are aligned (S1304). This correction is performed in the iterative operation of noise removal, to eliminate the deviation of the signal values of the input image and the output image, caused by the filter application.

Correction using the standard deviation employs Equation 1 to correct the image after filter application. In Equation 1, $\sigma_{before}$ is the standard deviation of the image calculated prior to the filter application (step S1303), and $\sigma_{after}$ is the standard deviation calculated after the filter application. In Equation 1, the ratio of the standard deviations before and after the filter application is taken as a coefficient, and each pixel of the image I (x, y) after the filter application is multiplied by the coefficient, to calculate the corrected image C (x, y).

Equation 1

$$C(x, y) = \frac{\sigma_{before}}{\sigma_{after}} I(x, y) \quad (1)$$

According to the present embodiment, the pre-processing for changing the size of the matrix by transforming the reconstructed image to the k-space data is not required, and the noise removal process is simplified. In particular, the method of applying the filter in the image space has the advantage that no additional Fourier transform is required. It should be noted that the technique of the present embodiment can also be combined with Embodiment 1. In that case, the pre-processing (FIG. 7) is performed prior to step S1201 shown in FIG. 12, and the post-processing (FIG. 8) is performed after step S1204. By combining with Embodiment 1 in this way, it is possible to further improve the image quality.

Figure 15:
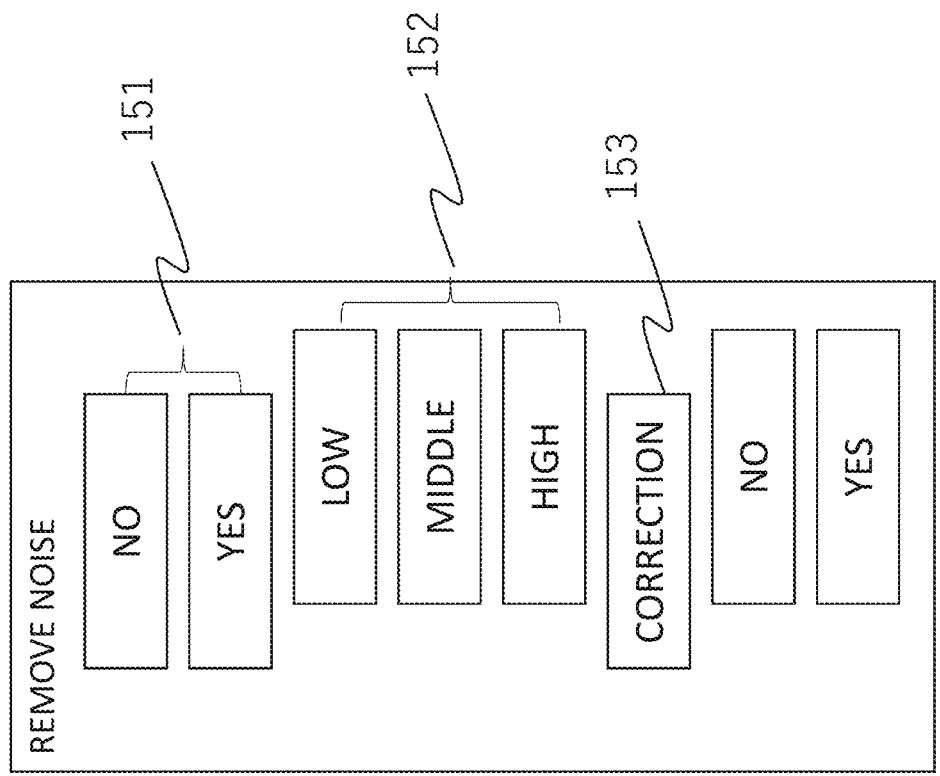
FIG. 15 illustrates an example of UI for user settings of noise removal.

Embodiments of the noise removal in the MRI apparatus according to the present invention has been described. Each of the embodiments described above may be incorporated alone in the MRI apparatus or in the image processor. Further, the need for noise removal, techniques thereof, or degrees of the noise removal may be user selectable. FIG. 15 illustrates an embodiment of a user interface (UI) for enabling the user selection.

Figure 6:
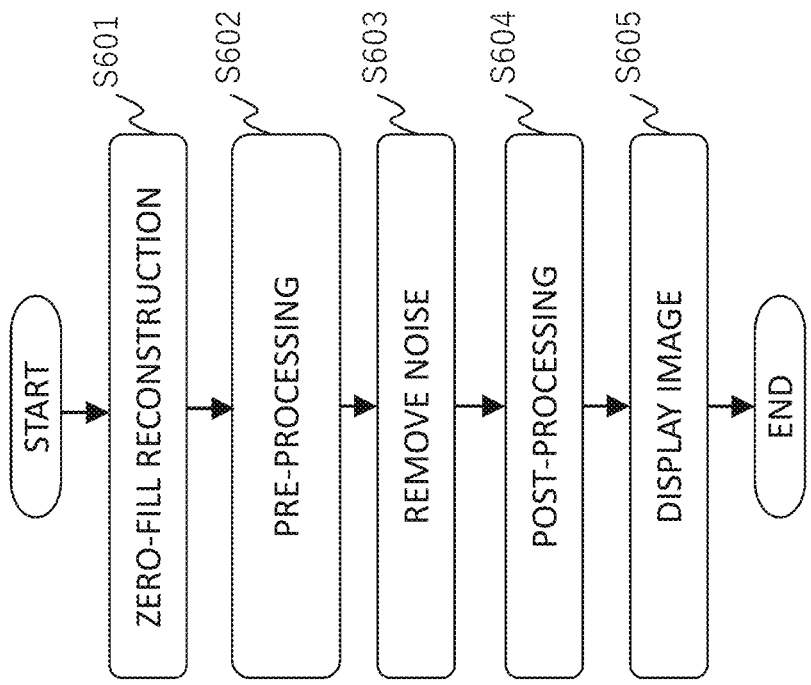
FIG. 6 is a flowchart of the processing of a noise remover according to a first embodiment.

For the user settings relating to the noise removal, for example, in the condition setting step S601 of FIG. 6, the display controller 240 displays the UI as shown in FIG. 15 on the display unit 201 and accepts the user selection. Here, UI may be constructed such that more than one technique may be selectable. In the example shown in FIG. 15, there are provided a button 151 for selecting whether to implement the noise removal, a button 152 for selecting the degree of noise removal (weak, medium, strong), and a button 153 for selecting whether to correct. For example, in the case of imaging of low zero-fill rate or imaging that prioritizes high speed, the user may omit the noise removal that relatively takes a time, whereas in the case of high zero-fill rate imaging, the user may set to perform the noise removal. The noise remover 230 may change, for example, the types and coefficients of the spatial filter created by the window function creating unit 238 of Embodiment 3, depending on the degree of noise removal set by the user. Also, only when the correction is required, the processing for eliminating artifacts (e.g., the pre-processing and the post-processing of Embodiments 1 and 2, and the filter processing of the Embodiment 3) is performed. This kind of UI provided can increase the flexibility in selecting the method by the user.

There have been described embodiments of the MRI apparatus and the image processing method for noise removal of the present invention. It should be noted that the present invention is not limited to the embodiments described above, and other noise removal techniques that do not contradict technically may be possible. For example, it is also possible to combine the addition of TV constraint conditions, or addition of different filters, and these are also encompassed by the present invention.

What is claimed is:

1. A magnetic resonance imaging apparatus comprising,
a measuring unit having a transmission unit configured to transmit an RF magnetic field pulse to a subject disposed in a static magnetic field;
a receiving unit configured to receive a nuclear magnetic resonance signal generated by the subject;
a gradient magnetic field generator for providing a gradient magnetic field to the static magnetic field; and
a computer configured to perform an operation on the nuclear magnetic resonance signal received by the receiving unit,
wherein the computer is programmed to:
process the nuclear magnetic resonance signal being received to generate a reconstructed image with a reconstruction matrix obtained by extending an acquisition matrix by zero-filling, remove noise from the reconstructed image after changing the size of a matrix of the reconstructed image by setting a mother wavelet as a reference and expanding/contracting and parallel translating the mother wavelet, thereby creating a noise-removed image, restore the matrix of the reconstructed image after the noise removal, to the reconstruction matrix, convert the noise-removed image from the image space data to k-space data by a Fourier transform, and cut out a reconstruction matrix size that is a same as a size prior the extending of the acquisition matrix in the k-space to obtain the reconstructed image.

2. The magnetic resonance imaging apparatus according to claim 1, wherein the computer is programmed to transform the matrix of the reconstructed image to a matrix larger than the reconstruction matrix.

3. The magnetic resonance imaging apparatus according to claim 2, wherein the computer is programmed to extend the matrix of the reconstructed image to the matrix larger than the reconstruction matrix, by zero-filling.

4. The magnetic resonance imaging apparatus according to claim 2, wherein the computer is programmed to extend the matrix of the reconstructed image to be four times larger than the acquisition matrix.

5. The magnetic resonance imaging apparatus according to claim 1, wherein, the computer is programmed to remove the noise after changing the matrix of the reconstructed image to be smaller than the reconstruction matrix, and restore the matrix of the reconstructed image after the noise removal to the reconstruction matrix.

6. The magnetic resonance imaging apparatus according to claim 5, wherein computer is programmed to use the size of the acquisition matrix, as the size of the matrix smaller than the reconstruction matrix.

7. The magnetic resonance imaging apparatus according to claim 5, wherein computer is programmed to use as the size of the matrix smaller than the reconstruction matrix, a value of power of two in a size equal to or larger than the acquisition matrix and smaller than the reconstruction matrix.

8. An image processing method for noise removal in an image acquired by a magnetic resonance imaging apparatus, the method comprising:

processing the acquired image to generate a reconstructed image obtained with a reconstruction matrix extended by zero-filling an acquisition matrix of nuclear magnetic resonance signals;

removing noise using an L1 norm minimization process from the reconstructed image after changing the size of a matrix of the reconstructed image and by setting a mother wavelet as a reference and expanding/contracting and parallel translating the mother wavelet, thereby creating a noise-removed image;

restoring the matrix size of the reconstructed image after the noise removal to an original size;

converting the noise-removed image from the image space data to k-space data by a Fourier transform; and cutting out a reconstruction matrix size that is a same as a size prior the extending of the acquisition matrix in the k-space to obtain the reconstructed image.

* * * * *